United States Patent
Yamauchi et al.

(10) Patent No.: US 9,435,786 B2
(45) Date of Patent: Sep. 6, 2016

(54) METHOD FOR DETERMINING DIFFERENTIATION LEVEL OF PLURIPOTENT STEM CELLS

(71) Applicant: HAMAMATSU PHOTONICS K.K., Hamamatsu-shi, Shizuoka (JP)

(72) Inventors: Toyohiko Yamauchi, Hamamatsu (JP);
Norikazu Sugiyama, Hamamatsu (JP);
Tadashi Fukami, Hamamatsu (JP);
Hidenao Iwai, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/023,735

(22) Filed: Sep. 11, 2013

(65) Prior Publication Data

US 2014/0073002 A1    Mar. 13, 2014

Related U.S. Application Data

(60) Provisional application No. 61/700,622, filed on Sep. 13, 2012.

(51) Int. Cl.
*C12Q 1/04*    (2006.01)
*G01N 33/483*   (2006.01)
*G01N 15/14*    (2006.01)
*G01N 15/10*    (2006.01)

(52) U.S. Cl.
CPC .......... *G01N 33/4833* (2013.01); *C12Q 1/04* (2013.01); *G01N 15/1456* (2013.01); *G01N 2015/1006* (2013.01); *G01N 2015/1497* (2013.01)

(58) Field of Classification Search
CPC ............. G01N 33/4833; G01N 2105/1006; G01N 2015/1497; G01N 15/1456; C12Q 1/04
USPC .......................................................... 435/34
See application file for complete search history.

(56) References Cited

FOREIGN PATENT DOCUMENTS

| JP | 4090244 B2 | 5/2008 |
| JP | 2010-048619 A | 3/2010 |
| JP | 2011-147400 A | 8/2011 |
| WO | WO-2011/043077 A1 | 4/2011 |
| WO | WO-2011/161962 A1 | 12/2011 |
| WO | WO-2012115153 A1 | 8/2012 |

OTHER PUBLICATIONS

Sugiyama et al., Label-free characterization of living human induced pluripotent stem cells by subcellular topographic imaging technique using full-field quantitative phase microscopy coupled with interference reflection microscopy. Biomedical Optics Express, vol. 3, No. 9 (Aug. 22, 2012) pp. 2175-2183.*

Mangoubi et al., "Non-Invasive Image Based Support Vector Machine Classification of Human Embryonic Stem Cells," Biomedical Imaging: From Nano to Macro, 2007. ISBI 2007. 4th IEEE International Symposium on, vol., No., pp. 284,287, Apr. 12-15, 2007.*

(Continued)

*Primary Examiner* — Kara Johnson
(74) *Attorney, Agent, or Firm* — Drinker Biddle & Reath LLP

(57) ABSTRACT

The present invention provides a method for determining differentiation level of pluripotent stem cell, comprising a step of determining a flatness of cultured pluripotent stem cell, wherein the flatness is an indication.

16 Claims, 10 Drawing Sheets

(56) References Cited

OTHER PUBLICATIONS

Nancy F. Glenn et al. "Analysis of LiDAR-derived topographic information for characterizing and differentiating landslide morphology and activity", Geomorphology, vol. 73, 2006, p. 131-p. 148.

Kaoru Mitsui et al., "The Homeoprotein Nanog Is Required for Maintenance of Pluripotency in Mouse Epiblast and ES Cells", Cell, vol. 113, 2003, p. 631-p. 642.

Ren-He Xu et al., "Basic FGF and suppression of BMP signaling sustain undifferentiated proliferation of human ES cells", Nature Methods, vol. 2(3), 2005, p. 185-p. 190.

Toyohiko Yamauchi et al., "Video-rate surface profiling of live cells by low-coherent reflection-type quantitative phase microscopy", Optics & Photonics Japan 2011 Conference Guide, 28aB1, 2011.

Toyohiko Yamauchi et al., "Long-term measurement of spontaneous membrane fluctuations over a wide dynamic range in the living cell by low-coherent quantitative phase microscopy", Proceedings of SPIE, vol. 8225, 2012, p. 82250A-1-p. 82250A-10.

Toyohiko Yamauchi et al., "Phase resolved and coherence gated en-face reflection imaging of multi-layered embryonal carcinoma cells", Proceedings of SPIE, vol. 8225, p. 82250G1-p. 82250G-10, (2012).

Notification of Transmittal of Translation of the International Preliminary Search Report on Patentability and Written Opinion issued Mar. 26, 2015 in International Application No. PCT/JP2013/071644.

Frank Gielsdorf & Tobias Hillmann, Springer Handbook of Geographc Information, (Wolfgang Kresse et al., eds., 2012) pp. 46-52.

DE Application No. 112013004463.3—Office Actiion dispatched Aug. 7, 2015.

Haupt, et al., Automated selection and collection of pluripotent stem cell colonies using the CellCelector, Nature Methods, Jun. 2009, pp. III-IV.

Takashi, et al., Induction of Pluripotent stem cells from fibroblast cultures, Nature Protocols, 2007, vol. 2, No. 12, pp. 3081-3089.

\* cited by examiner (a)

(b)

(c)

(d)

(a)

(b)

METHOD FOR DETERMINING DIFFERENTIATION LEVEL OF PLURIPOTENT STEM CELLS

CROSS-REFERENCE TO RELATED APPLICATION

This application claims priority to Provisional Application (61/700,622) filed on Sep. 13, 2012, which is hereby incorporated by reference in its entirety.

BACKGROUND OF THE INVENTION

1. Technical Field

The present invention relates to a method for determining differentiation level of pluripotent stem cells.

2. Background Art

An embryonic stem cell has a pluripotency to differentiate into various cells, so that its application to repair or regeneration of various tissues is expected in the field of regenerative medicine, for example. Since cells derived from a fetus are used, however, its practical application in the medicine is presumably difficult because of limited cell source, controversial ethical questions, and the like. In order to solve such problems, an induced Pluripotent Stem cell (hereinafter also referred to as "iPS cell") has been developed. An iPS cell is a pluripotent stem cell artificially induced from an adult cell, which has an ability of self-replication and pluripotency. Since an iPS cell is induced from an adult cell, the cell source is relatively more abundant than that of an embryonic stem cell, and further there are few ethical questions, which makes its application in the regenerative medicine or the like more suitable.

SUMMARY OF THE INVENTION

However, an iPS cell is different from an established cultured cell in that the iPS cell tends to nonspecifically and easily differentiate into a more mature cell during a subculture. Since a differentiated iPS cell gradually becomes unable to be continuously cultured and further loses pluripotency, there is a problem that it becomes less and less suitable for application in regenerative medicine or the like. Therefore, when culturing iPS cells, cellular quality control by determining their differentiation level to remove cells with an inappropriate differentiation level is required.

Conventionally, a method for determining the differentiation level by visual observation based on a phase contrast microscopic image is known; however, a phase contrast microscope lacks quantitativity and thus does not accurately reflect the differentiation level of cells.

In addition, as a method for determining the differentiation level of cells more accurately, a method in which cells are stained with an antibody and a method in which cells are stained with an alkaline phosphatase or the like, as disclosed in, for example, Mitsui, K. et al., Cell 113 (2003): 631-642, are generally known. However, these methods require destroying the cells. In addition, as a method for determining cells alive, a method in which specific cell surface markers are recognized with an antibody labeled with a fluorescent label or the like, and, as disclosed in, for example, Xu, R. et al., Nature Methods 2 (2005): 185-190, a method in which cells are recognized with an antibody against an undifferentiated marker and measured using FACS are known. However, a pluripotent stem cell such as an iPS cell is sensitive to environmental change, and an external reagent such as a fluorescence reagent may affect the differentiation and nature of the pluripotent stem cell. Furthermore, in case of applying such a cell in the regenerative medicine or the like and transplanting the cell into a human body, a risk for contamination of external reagents or the like and pollution due to the complexity of operation should be avoided. Therefore, a method for determining the differentiation level in an unstained and noninvasive manner is required.

The present invention, in view of the above-mentioned circumstances, aims to provide a method for determining the differentiation level of cells without using staining and noninvasively.

The present inventors have found that the surface of cultured undifferentiated pluripotent stem cell is flatter than that of differentiated cell. Based on the above findings, the inventors have completed the present invention.

Specifically, the present invention relates to a method for determining the differentiation level of a pluripotent stem cell, of which flatness is an indication. The above-mentioned determining method comprises a step of determining flatness of a cultured pluripotent stem cell. In the above-mentioned determining method, the flatness is an indication of the differentiation level, and specifically, as a surface of one cell or a surface of a cell population is more flat, the cell is less differentiated, and as the surface of the cell or the surface of the cell population is less flat, the cell is more differentiated. Therefore, using the above-mentioned determining method, whether an undifferentiated pluripotent stem cell or a differentiated pluripotent stem cell can be determined, and further the differentiation level can be determined. Note that in the specification, the flatness is flatness of a surface of one cell or flatness of a surface of a cell population.

The flatness of the surface of the cell population may be specifically flatness in a microscopic visual field unit, or may be flatness in a region of interest unit (hereinafter also referred to as "ROI") within a microscopic visual field.

The flatness of the surface of the cell population may be specifically a flatness in a microscopic visual field unit, or may be a flatness in a region of interest unit (hereinafter also referred to as "ROI") within a microscopic visual field.

Using the flatness in a microscopic visual field unit, the differentiation level in the whole culture system can be determined, and the flatness can also be determined more easily and effectively and the differentiation level can be determined more effectively.

Using the flatness in a region of interest unit within a microscopic visual field allows increasing the number of samples easily.

The flatness may also be flatness of a cell (one cell). For cells in a microscopic visual field, using the flatness of each cell, the flatness can be determined in a more accurate physiological nature-based manner, and thus the differentiation level can be determined more accurately.

The flatness may also be a standard deviation of height of the surface of the cell or the surface of the cell population. In accordance with this, the flatness can be determined easily. Note that the height of the surface of the cell is a distance from a bottom surface of the cell attaching to a culture vessel to a surface of the cell not attaching to the culture vessel, and the height of the surface of the cell population is a distance from a bottom surface of the cell population attaching to a culture vessel to a surface of the cell population not attaching to the culture vessel.

The flatness may also be a value of mean square height difference (hereinafter also referred to as "MSHD") in a predetermined horizontal distance. In accordance with this, a value of the flatness in which a position of the object in the space is reflected can be obtained, thereby determining the differentiation level of pluripotent stem cell more accurately.

Furthermore, the flatness may also be a slope of a variogram in a horizontal distance between predetermined two points. In accordance with this, a determining method of differentiation level of pluripotent stem cell with superior determination ability can be provided.

The flatness may be standardized with a mean value of height of the surface of the cell or the surface of the cell population. In accordance with this, an influence by difference in an average height of the surface of the cell or the cell population can be corrected.

The flatness may be determined using a reflection quantitative phase microscope. In accordance with this, a three-dimensional cell shape can be obtained with the resolving power being equal to or less than 1 micron.

DESCRIPTION OF THE PREFERRED EMBODIMENTS

Hereinafter, description is made for some preferred embodiments of the present invention in detail.

The present invention provides a method for determining differentiation level of pluripotent stem cell, of which a flatness is an indication, comprising a step of determining the flatness of the cultured pluripotent stem cell.

According to the present invention, using a distinctive characteristic, the inventors have found, that cultured undifferentiated pluripotent stem cell is flatter than differentiated cell, the differentiation level of cultured pluripotent stem cell can be determined.

Figure 1:
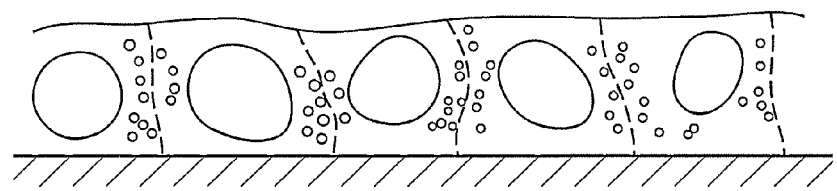
FIG. 1 is schematic views of vertical sections of (a) undifferentiated pluripotent stem cell, and (b) to (d) differentiation-induced pluripotent stem cell.
Figure 1:
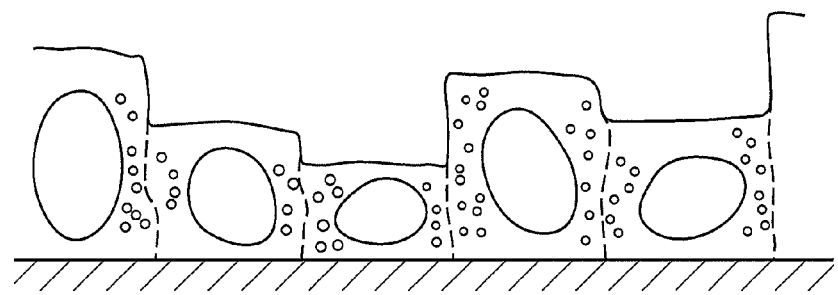
Figure 1:
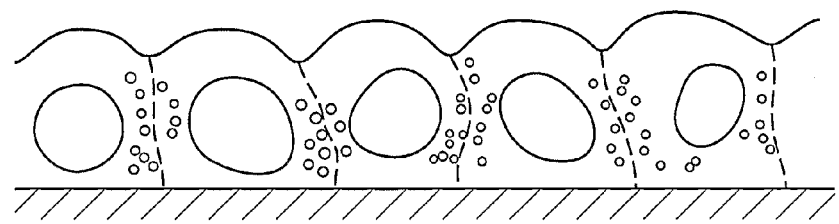
Figure 1:
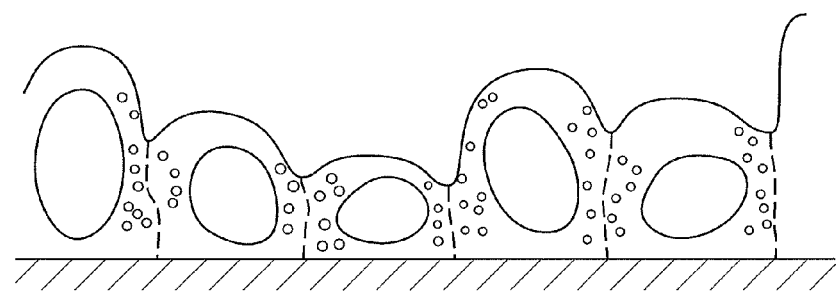

The flatness of undifferentiated pluripotent stem cell and differentiation-induced pluripotent stem cell is described referring to FIG. 1 that is schematic views of the vertical sections. As to the undifferentiated pluripotent stem cell, as shown in FIG. 1a, the surface of the cell or the surface of the cell population is flat. On the other hand, the surface of the pluripotent stem cell in which differentiation has been induced by addition of retinoic acid, for example, become not flat, and as shown in FIG. 1b, although the flatness of the surface of the cell is maintained in the individual cells, the flatness between the cells may be destroyed in one visual field or one colony. In addition, as shown in FIG. 1c, the surface may not be flat in the individual cells. In fact, the inventors have found that inducing differentiation of pluripotent stem cell causes a change from a state of FIG. 1a to a state of FIG. 1b and a change therefrom to a state of FIG. 1c in parallel, and brings the cells into a state of FIG. 1d.

Using the determining method of the present invention, the differentiation level of cell can be determined in an unstained and noninvasive manner. The differentiated cell can be removed on a cell-by-cell, colony-by-colony or dish-by-dish basis, allowing easy control of the cellular quality of pluripotent stem cells.

In the specification, a kind of pluripotent stem cell is not limited in particular, as long as the cell has the nature of stem cell, that is, abilities to divide forever in culture and to differentiate into one or more cell types. Such a cell may be a naturally occurring stem cell or may be an iPS cell. In addition, the above-mentioned pluripotent stem cell may be derived from a fetus, or may be an adult tissue-derived stem cell such as a small intestine epithelium stem cell, a precursor cell of any cell type and an iPS cell induced from an adult cell. From the viewpoint of cell source and ethics, the pluripotent stem cell is preferred to be a cell except an embryonic stem cell, more preferred to be an iPS cell.

The ability of the pluripotent stem cell for differentiation is not limited in particular, as long as the cell has an ability to differentiate into one or more cell types. In other words, examples of the pluripotent stem cell include a totipotent embryonic stem cell, stem cells of various organs and cell types, and precursor cells of various cell types.

It is preferable for the iPS cell to be induced from an adult cell of an animal, more preferable to be induced from an adult cell of a mammal such as a mouse, a rat and a human, and further preferable to be induced from an adult cell of a human.

A cell type and tissue from which the iPS cell is derived are not limited in particular, and the examples thereof include a fibroblast, a skin epithelial cell and a hemopoietic precursor cell.

A preparing method of the iPS cell is not limited in particular. An iPS cell may be induced by introducing an iPS cell inducer such as a gene cluster consisting of OCT3/4, SOX2, KLF-4 and C-MYC genes and a gene cluster consisting of OCT3/4, SOX2 and KLF-4 genes.

The differentiation, as used herein, refers to a process of progressive transformation by which a cell acquires biochemical and morphological properties required to perform a specialized function. The differentiation level, as used herein, refers to an extent of progression of differentiation from a totipotent embryonic stem cell to an adult cell having no ability for differentiation, that is a terminally differentiated cell, in any adult. Although such a differentiation level varies for each cell and each tissue, a person skilled in the art can appropriately decide the criteria in accordance with the application purpose or the like. Note that the undifferentiated cell refers to a cell with a lower differentiation level, that is, a cell with higher ability for differentiation, and the differentiated cell refers to a cell with a higher differentiation level, that is, a cell with lower ability for differentiation.

The above-mentioned pluripotent stem cell is a pluripotent stem cell cultured in vitro in a culture dish, on a cover glass or the like, and preferably a pluripotent stem cell cultured in a culture dish made of glass. In addition, it is preferable for the surface of the culture dish to be coated with an antireflective coating. This enables to suppress influence of optical reflection from glass, when observing or measuring the cells through a microscope or the like.

The flatness can be determined as flatness for one cell. In this case, the flatness can be determined by shooting tomograms at intervals of 1 μm at least in the vertical direction in one cell to produce cross sectional layers and extracting the surface shape to make a data processing. Physiological natures of the cell can be determined more accurately by determining the flatness for each cell in a visual field.

The flatness can also be determined as flatness for a cell population comprising a plurality of cells, for example, in a visual field unit or for a ROI unit within a visual field. In this case, the flatness can be determined by shooting tomograms at intervals of 1 μm at least in the vertical direction in one cell population to produce cross sectional layers and extracting the surface shapes to perform data processing.

The flatness can also be determined as a flatness for a cell population comprising a plurality of cells, for example, for a visual field unit or for a ROI unit within a visual field. In this case, the flatness can be determined by shooting tomograms at intervals of 1 μm at least in the vertical direction in one cell population to produce cross sectional layers and extracting the surface shapes to perform data processing.

A person skilled in the art can appropriately determine the range of the number of cells constituting the cell population in accordance with the origin of pluripotent stem cells, culture condition, application purpose or the like. When the pluripotent stem cells are iPS cells derived from human adult fibroblasts, such a cell population is a cell population preferably comprising at least 20 cells, and more preferably comprising at least 50 cells. Selection of such a cell population enables avoiding the bias caused by cells in an extreme state in the culture system.

By determining the flatness for a visual field unit information can be easily obtained from a large number of cells and the differentiation level of pluripotent stem cells is easily determined in the whole culture system. In this case, in order to enhance the reliability, decision of the flatness for one cell population is made for preferably at least 4 visual fields, and more preferably at least 7 visual fields.

Examples of the approach for sampling visual fields in a cell population to be shot include a random sampling method in which the visual fields are randomly picked up around the center and a sequential sampling method in which the visual fields are sequentially transferred in one direction. Using the random sampling method allows more easily determining the differentiation level of pluripotent stem cells in the whole culture system. Using the sequential sampling method allows more accurately determining the differentiation level of pluripotent stem cells constituting the whole cell population.

By determining the flatness for a ROI unit within a visual field, information can be obtained more easily from many cell populations and the differentiation level of cells can be determined more accurately. In this way, by only performing a sampling inspection, the differentiation level of pluripotent stem cells can be determined in the whole culture system. In addition, by partitioning a visual field into a plurality of ROIs, an analysis can be performed for each ROI units that can be set regardless of the device specification, thereby enhancing the versatility.

When the flatness for a ROI unit within a visual field is determined, a person skilled in the art can appropriately determine the size of ROI and the number of partitions in one visual field in accordance with the origin of pluripotent stem cells, culture condition, application purpose or the like. From the viewpoint of the reliability and physiological meaning, the size of ROI is preferably around a size of the cell. When the pluripotent stem cells are iPS cells derived from a fibroblast, it is preferable for the size of ROI to be around 10 μm×10 μm to 30 μm×30 μm, and more preferable to be 23 μm×23 μm. In addition, it is desirable for the size of one visual field to have a sufficient area to include six or more ROIs, and more preferable to be 80 μm×60 μm or more.

When the differentiation level of pluripotent stem cell is determined based on the flatness as an indication, it is shown that the more flat the surface of the cell or the surface of the cell population is more flat, the cell is less differentiated the cell, and the less flat the surface of the cell or the surface of the cell population is less flat, the cell is more differentiated the cell. The flatness may be confirmed by microscopy, but the calculation and numerical conversion are preferable for an objective evaluation. A calculation method of the flatness is not limited in particular, as long as the method can distinguish the flatness of undifferentiated pluripotent stem cell from that of differentiated cell. Examples of such a method include a calculation method described below. Note that, unless otherwise specified, the description of the cell includes a cell population, the description of a surface of the cell includes a surface of a cell population, and the description of a bottom surface of the cell includes a bottom surface of a cell population.

The flatness may be calculated as a standard deviation of height of the surface of the cell. In this case, as the numerical value is smaller, the cell is more flat and less differentiated, and as the numerical value is larger, the cell is less flat and is more differentiated. The flatness can be easily calculated using this method.

The flatness may also be a value of MSHD in a predetermined horizontal distance. When a surface shape Z (x, y) is given and two points, A $(x_1, y_1)$ and B $(x_2, y_2)$, which are apart from each other at a Δr in the horizontal direction on the Z, are selected, the MSHD can be represented by formula (I).

$$MSHD(\Delta r) = \langle (z(x_1,y_1) - z(x_2,y_2))^2 \rangle \quad (I)$$

wherein z $(x_1, y_1)$ is a height of a surface of the cell at A, z $(x_2, y_2)$ is a height of a surface of the cell at B, and $\langle \rangle$ is an ensemble average. In addition, $(x_1, y_1)$ and $(x_2, y_2)$ are in any combination that satisfies formula (II).

$$\Delta r = ((x_1-x_2)^2 + (y_1-y_2)^2)^{1/2} \quad (II)$$

By calculating the flatness as a value of MSHD in a predetermined horizontal distance, a value of the flatness in which a position of the object in the space is reflected can be obtained, and the differentiation level of pluripotent stem cell can be determined more accurately. In this case, as the numerical value is smaller, the cell is more flat and less differentiated, and as the numerical value is larger, the cell is less flat and is more differentiated.

Represented as a function of MSHD in a horizontal distance is generally called a variogram. That is, when a surface shape Z (x, y) is given and two points, A $(x_1, y_1)$ and B $(x_2, y_2)$, which are apart from each other at a Δr in the horizontal direction on the Z, are selected, although point A and point B may be selected in several ways, the ensemble average of the square of the difference between the heights that are selected in that way becomes the variogram. A variogram is used, as described in Glenn, N. et al., Geomorphology 73 (2006): 131-148, for example, as an indication in which the flatness of surface shape is numerically converted, in the surface shape analysis of topography or SEM image, fractal analysis or the like.

The Δr is not limited in particular, as long as the Δr is between points enough to definitely determine the difference between undifferentiated pluripotent stem cell and differentiated cell. A person skilled in the art can appropriately determine the Δr in accordance with the origin of pluripotent stem cell, application purpose or the like.

The flatness may also be a slope of a variogram in a horizontal distance between the predetermined two points. In this case, as the numerical value is smaller, the cell is flatter and less differentiated, and as the numerical value is larger, the cell is less flat and is more differentiated. The horizontal distance between the predetermined two points is not limited in particular, as long as the distance is between points enough to definitely determine the difference between undifferentiated pluripotent stem cell and differentiated cell. The relationship between a mean square height difference and a slope of a variogram can be represented by formula (III).

$$MSHD(\Delta r) \propto \Delta r^S \quad (III)$$

wherein S is a slope of a graph which represents a variogram in a double logarithmic manner. It should be noted that because of the nature of a log-log graph, even when constantly multiplying the abscissa Δr or ordinate MSHD through the standardization, the graph is only translated parallelly and the slope S is constant with respect to the constantly multiplied abscissa and ordinate. In addition, as shown in the above-mentioned document of Glenn, N. et al., it is a known mathematical approach to represent a variogram by log-log graph and evaluate the statistical nature of the surface shape by slope S.

It is preferable for the flatness to be standardized, for example, with a mean value of height of the surface of the cell. This enables correcting influence by the height difference of the surface of the cell between cells or cell populations, thereby not only representing the more accurate differentiation level, but also comparing and determining the differentiation levels among a plurality of cells or cell populations.

A method for determining the differentiation level is described more specifically. Examples of such a method include a method which can make determination in which undifferentiated pluripotent stem cells are considered as a positive control to be compared with cells targeted for determination. In this case, when the cell targeted for determination is as flat as, or flatter than the positive control of the pluripotent stem cells, it can be determined that the cell targeted for determination is undifferentiated.

In addition, there is also a method in which differentiated cells are considered as a negative control to be compared with cell targeted for determination. In this case, when the cell targeted for determination is as flat as, or not flatter than the negative control of the cells, it can be determined that the cell targeted for determination is differentiated.

Furthermore, there is another determining method in which the flatness of undifferentiated pluripotent stem cells as a positive control and the flatness of differentiated cells as a negative control are individually calculated beforehand, and a standard value for determination can be set based thereon. A person skilled in the art can appropriately determine such a standard value for determination in accordance with the origin of pluripotent stem cell, culture condition, application purpose or the like.

Note that a person skilled in the art can appropriately determine the cells for the positive and negative controls in accordance with the application purpose of pluripotent stem cell or the like, for example, a person skilled in the art can consider the undifferentiated pluripotent stem cells as a positive control and the terminally differentiated pluripotent stem cells as a negative control. These cells are preferably derived from the same cell type, and more preferably derived from the same undifferentiated pluripotent stem cell. In addition, a person skilled in the art can appropriately decide such a determining method, standard value for determination and the like in accordance with the application purpose or the like.

A method for extracting the surface shape of a cell is not limited in particular, but in order to accurately represent the cell shape, a method using an three-dimensional imaging device is preferable. This can solve a problem, caused in using a conventional phase contrast microscope, in that intracellular materials refract transmitted light, and can measure the cell surface accurately.

In addition, it is more preferable for the three-dimensional imaging device to be noninvasive three-dimensional imaging devices, among them, further preferable to be a quantitative phase microscope, low coherence interference microscope, tomographic phase microscope and scanning probe microscope, particularly preferable to be a reflection quantitative phase microscope, and extremely preferable to be a reflection low coherence quantitative phase microscope. By using these devices, a risk for the influence and contamination on pluripotent stem cells can be minimized, which is superior from the viewpoint of medical application.

Examples of the quantitative phase microscope include those disclosed in Japanese Patent No. 4090244 and Japanese Patent Application Laid-Open Publication No. 2010-48619. By using the quantitative phase microscope, an optical field strength and phase can be quantitatively measured using the phase-shifting interferometry. In addition, from the viewpoint of correct measuring of a cell surface, it is preferable to be a reflection quantitative phase microscope. By using the reflection quantitative phase microscope, a three-dimensional image of the cell shape can be obtained with the resolving power being equal to or less than 1 micron.

Using the low coherence interference microscope allows probing a certain sectional plane in a cell, in which adjusting a longitudinal position of a coherence gate on a cell membrane allows only light reflected by the cell membrane to be involved in the interference, regardless of the intracellular structure.

By using the tomographic phase microscope, a three-dimensional image of a cell shape can be reconstructed.

By using the scanning probe microscope, a distance between a bottom surface of a cell and a surface of a cell can be measured directly.

By using the reflection low coherence quantitative phase microscope, the surface shape of a cell can be extracted with a high degree of accuracy. Examples of the reflection low coherence quantitative phase microscope include those disclosed in Yamauchi T. et al., Proc. of SPIE Vol. 8225: 82250G-1 and Yamauchi T. et al., Proc. of SPIE Vol. 8225: 82250A-1.

EXAMPLES

Hereinafter, description is made of the present invention with reference to some examples more specifically, but the present invention should not be limited to these examples.

Example 1

Onto an antireflectively coated glass bottom dish with 35 mm diameter, a 253G1 iPS cell line derived from a human adult fibroblast was seeded at 10 to 20 colonies/dish and cultured on feeder using a Primate ES Medium (manufactured by ReproCELL Incorporated, a commercial name: RCHEMD001) containing 4 ng/mL human basic FGF in the final concentration. The size of one colony was around 200 µm. As the feeder cells, mouse lung fibroblasts were used. The cells were cultured until the third day after the seeding. The medium was replaced once a day.

A sample of the iPS cells for differentiation, the medium of which was replaced with a Primate ES Medium containing 4 ng/mL human basic FGF and 12.5 µM retinoic acid in the final concentration on the second day after the seeding, was cultured for another 4 days. Retinoic acid is generally used as a reagent for inducing differentiation. In addition, for a control of differentiated cells, MCF7 cells were used which were human breast cancer-derived epithelial cells. The MCF7 cells were seeded at 20% cell density and cultured for 3 days to be approximately confluent using 10% FBS-containing DMEM medium. In each culture system except the MCF7 cell culture system, the medium was replaced once a day.

The shape of the cells was observed using a reflection quantitative phase microscope. Schematic views of the vertical sections of the cells were shown in FIG. 1. The cell surfaces of the iPS cells cultured by supplementing retinoic acid were not flat, which had the surface shape as shown in FIGS. 1b to 1d. In contrast to this, the cell surfaces of the undifferentiated iPS cells were relatively flat, which had the surface shape as shown in FIG. 1a.

In the following examples, as an indication of the flatness, four indexes of a value of a standard deviation of height of the surface of the cell which is standardized with a mean value of height of the surface of the cell, a value of MSHD which is standardized with a mean value of height of the surface of the cell, a variogram which is standardized with a mean value of height of the surface of the cell, and a slope of the variogram are shown. In these four indexes, as mentioned above, it is shown that as the value is smaller, the cell and cell population are flatter, and as the value is larger, the cell and cell population are not flatter.

Figure 2:
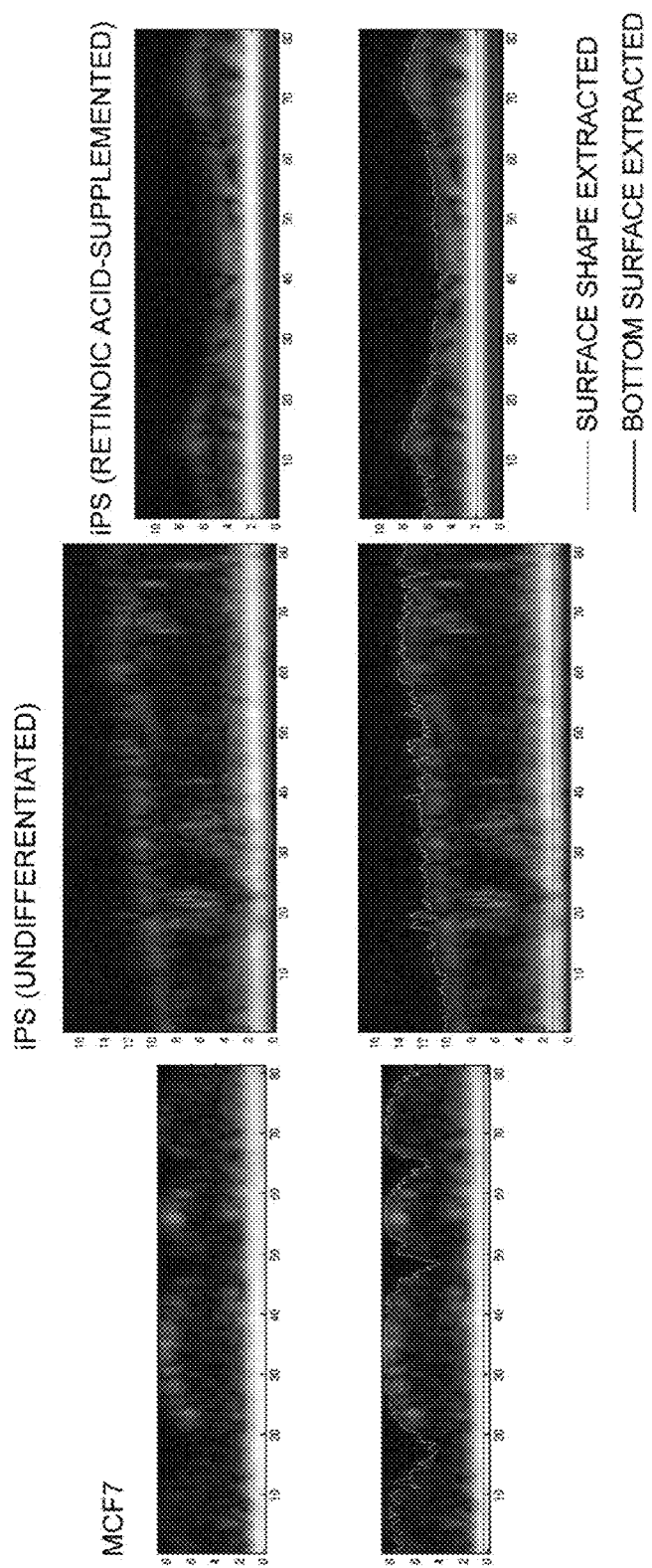
FIG. 2 is views showing bottom surfaces and surface shapes of cells extracted from tomographic images with three-dimensional data obtained by shooting three-dimensional images of the cells in a 60 μm×80 μm visual field using a reflection quantitative phase microscope in Example 1. The cells used were MCF7 cells, undifferentiated iPS cells and iPS cells cultured by supplementing retinoic acid.
Figure 3:
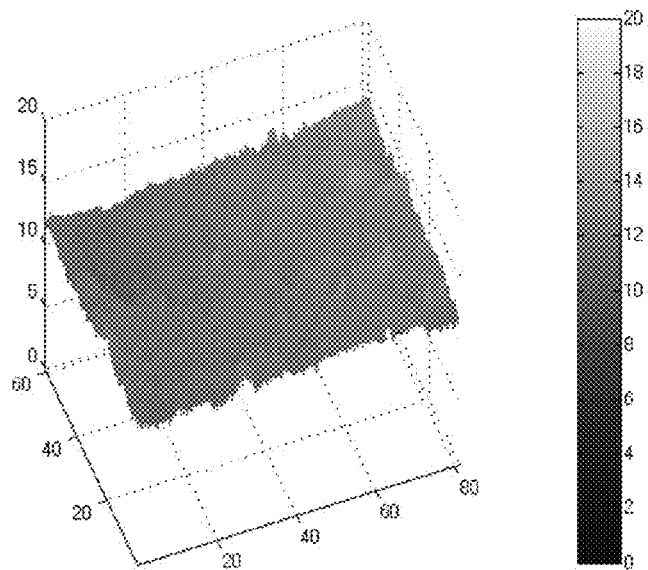
FIG. 3 is views in which three-dimensional images of cells in a 60 μm×80 μm visual field shot using a reflection quantitative phase microscope in Example 1 are numerically converted and plotted. The cells used were undifferentiated iPS cells and iPS cells cultured by supplementing retinoic acid.
Figure 3:
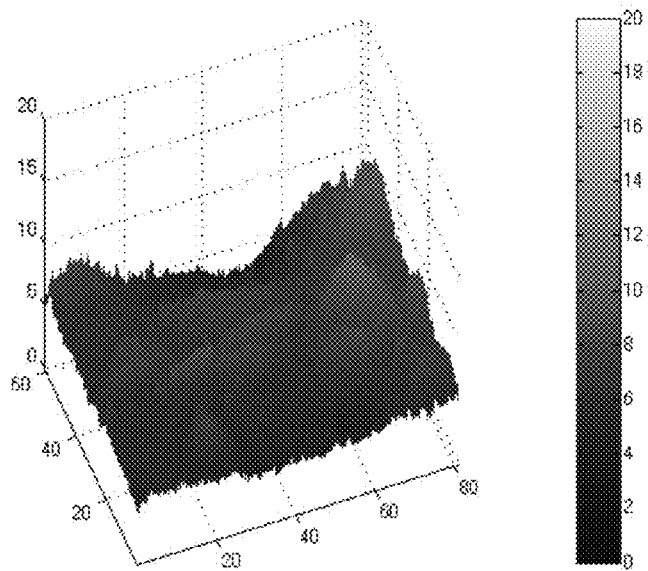

The bottom surface and surface shapes of the cell were extracted as follows. By using a reflection quantitative phase microscope, three-dimensional data for the cells in a 60 µm×80 µm visual field were obtained every 0.125 µm in the horizontal direction and every 0.32 µm in the vertical direction, and from the obtained data, tomogram images were created. From the created tomogram images, as shown in FIGS. 2 to 3, the bottom surface and surface shapes were extracted and numerically converted. By performing this processing in the whole visual field, the bottom surfaces and surface shapes in the whole visual field were obtained. From the obtained bottom surfaces and surface shapes, the height of the surface of the cells was measured. The flatness was calculated as a standard deviation of height of the surface of the cells which was standardized with a mean value of height of the surface of the cells, and a statistical processing was done. The calculated flatness of each sample was shown in Table 1. The flatness of the iPS cells cultured by supplementing retinoic acid was higher than the flatness of the undifferentiated iPS cells, and lower than the flatness of the MCF7 cells.

TABLE 1

|  | Mean value of height of the surface of the cells (µm) | Standard deviation of height of the surface of the cells | Flatness (%) |
| --- | --- | --- | --- |
| Undifferentiated iPS cells | 12.3 | 0.72 | 5.85 |
| Retinoic acid-added iPS cells | 6.25 | 1.18 | 18.9 |
| MCF7 | 5.80 | 1.66 | 28.6 |

Example 2

Figure 4:
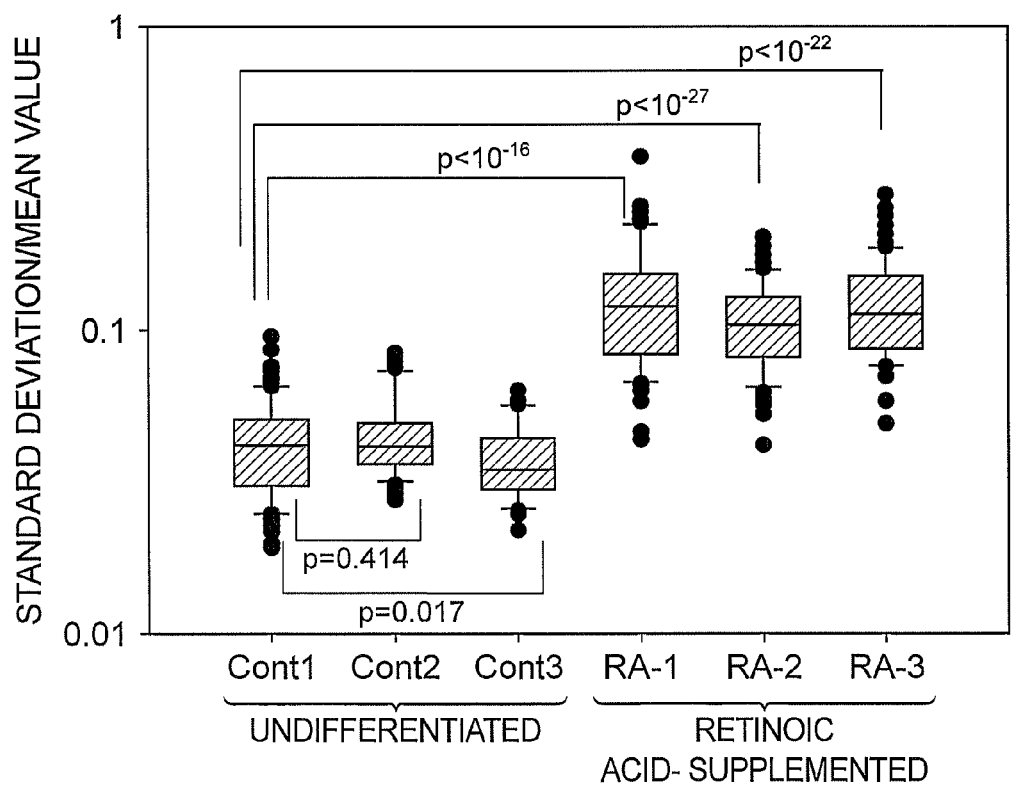
FIG. 4 is a view showing the flatness of undifferentiated iPS cells and iPS cells cultured by supplementing retinoic acid in Example 2. The flatness was calculated as a standard deviation of height of the surface of the cell, which was standardized with a mean value of height of the surface of the cell in a ROI unit within a microscopic visual field.

As to 3 colonies of the undifferentiated iPS cells and 3 colonies of the iPS cells cultured by supplementing retinoic acid, 7 to 15 visual fields around the center of each colony were analyzed. Each visual field was partitioned into six ROIs, and the bottom surfaces and surface shapes of the cells were extracted for each ROI unit to measure the height of the surface of the cells under the same condition as that of Example 1. The size of the ROI was 23 µM×23 µm. The flatness was calculated as a standard deviation of height of the surface of the cells which was standardized with a mean value of height of the surface of the cells, and a statistical processing was done to perform Student's t-test. The result was shown in Table 2 and FIG. 4. The flatness of the iPS cells cultured by supplementing retinoic acid was higher than the flatness of the undifferentiated iPS cells, in which the difference was significant.

TABLE 2

|  | Undifferentiated iPS cells | | | Retinoic acid-added iPS cells | | |
| --- | --- | --- | --- | --- | --- | --- |
|  | Cont-1 | Cont-2 | Cont-3 | RA-1 | RA-2 | RA-3 |
| Flatness | 0.043 | 0.045 | 0.038 | 0.130 | 0.107 | 0.123 |
| Standard deviation | 0.016 | 0.014 | 0.011 | 0.062 | 0.034 | 0.047 |

Example 3

Figure 5:
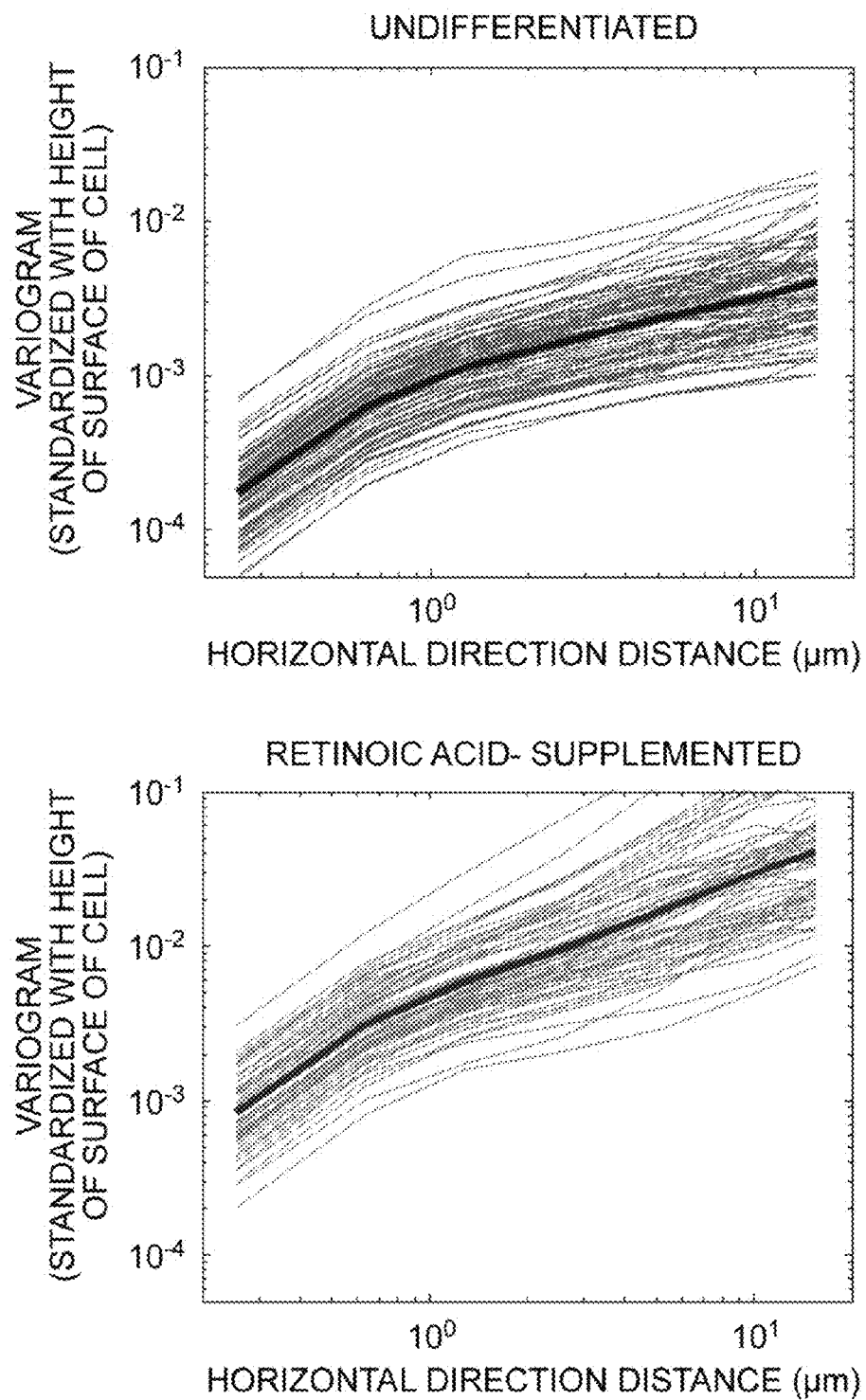
FIG. 5 is views showing variograms which are standardized with a mean value of height of the surface of the cell of undifferentiated iPS cells and iPS cells cultured by supplementing retinoic acid in Example 3. The measurement was performed for a ROI unit in a microscopic visual field.

Under the same condition as that of Example 2, three-dimensional data for the undifferentiated iPS cells and the iPS cells cultured by supplementing retinoic acid were obtained every 0.125 μm in the horizontal direction and every 0.32 μm in the vertical direction, and from the obtained data, tomogram images were created. From the created tomogram images, the bottom surfaces and surface shapes of the cells were extracted and a variogram analysis was performed. Specifically, a value of MSHD when the Δr was within a range of 0.25 μm to 15 μm was calculated from formula (I) as described above, and standardized with a mean value of height of the surface of the cells. As shown in FIG. 5, the flatness of the iPS cells cultured by supplementing retinoic acid was higher than the flatness of the undifferentiated iPS cells.

Figure 6:
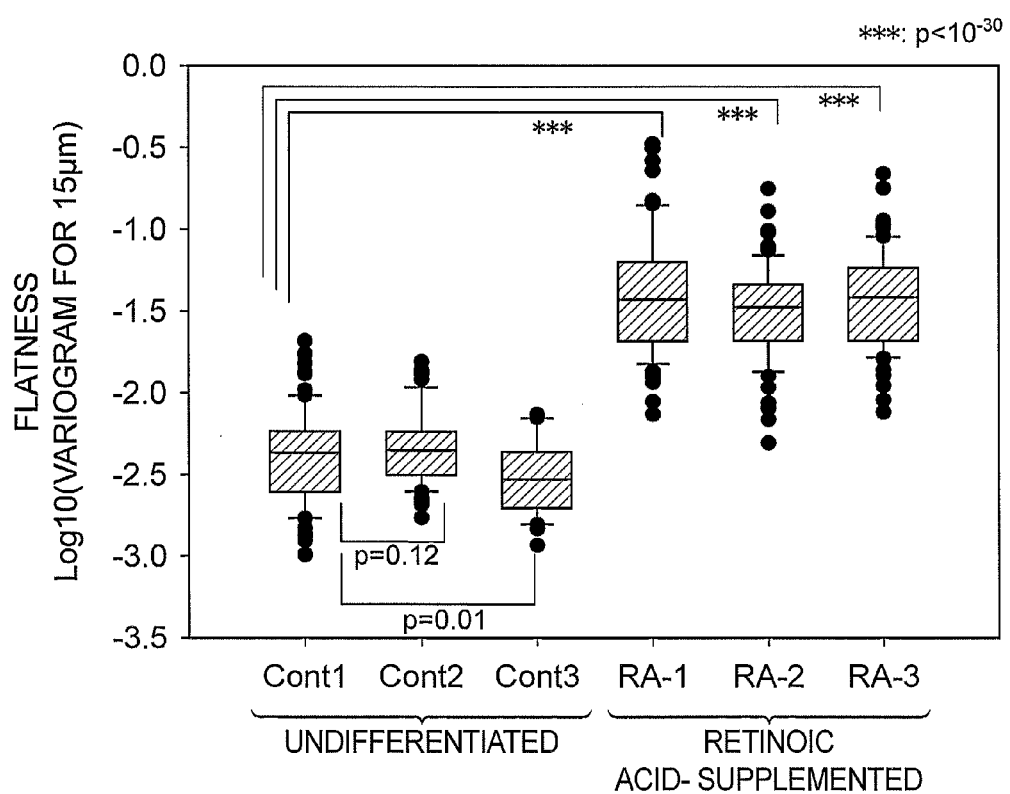
FIG. 6 shows the result from an analysis of variograms for undifferentiated iPS cells and iPS cells cultured by supplementing retinoic acid in Example 3. The flatness was calculated as a value of MSHD when the horizontal distance ($\Delta r$) was 15 μm, which was standardized with a mean value of height of the surface of the cell.
Figure 7:
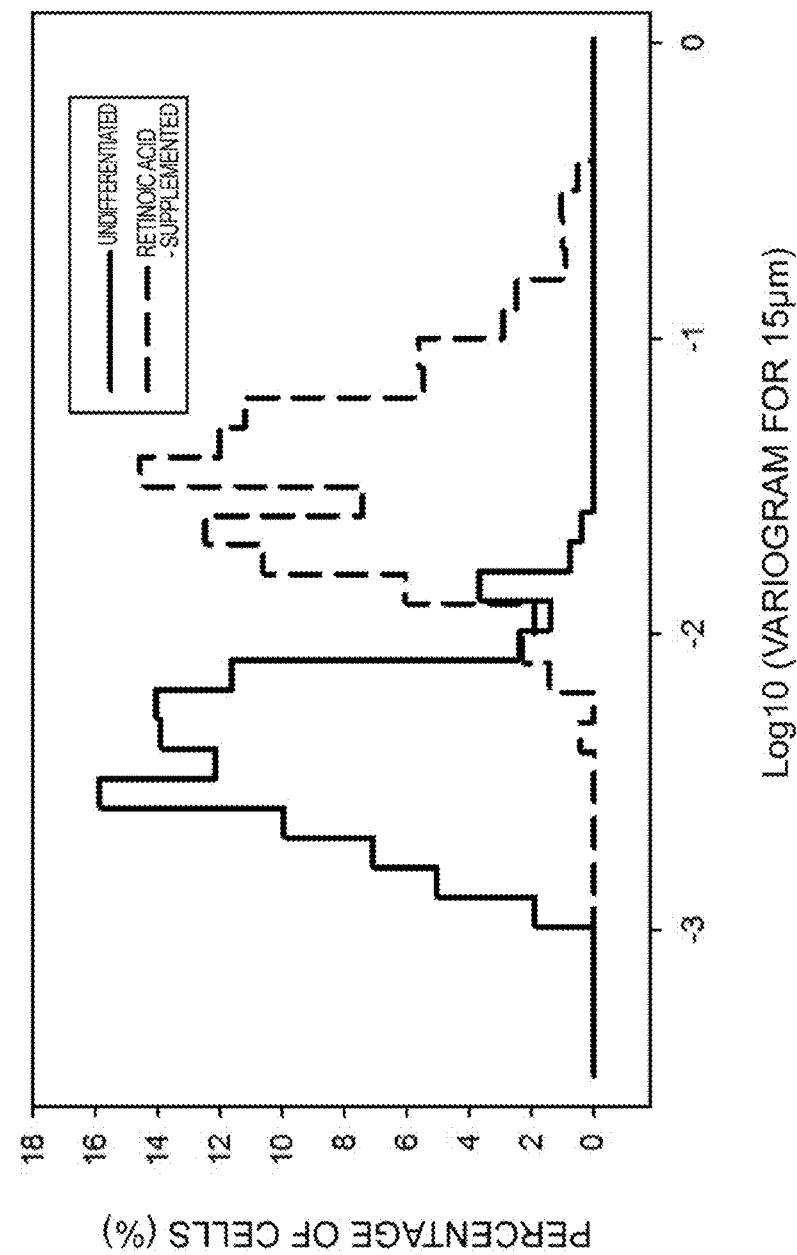
FIG. 7 is a histogram obtained from an analysis of variograms for undifferentiated iPS cells and iPS cells cultured by supplementing retinoic acid (3 colonies each), which are standardized with a mean value of height of the surface of the cell when considering all the cells as a population in Example 3. The $\Delta r$ is 15 μm.

Next, a value of MSHD when the Δr was 15 μl was calculated and standardized with a mean value of height of the surface of the cells to calculate the flatness. The result was shown as a logarithmic graph (FIG. 6). In a statistical analysis, the common logarithm of the result was calculated to perform Student's t-test (Table 3). The flatness of the iPS cells cultured by supplementing retinoic acid was markedly higher than the flatness of the undifferentiated iPS cells. In addition, considering all of the colonies 1 to 3 in each group (i.e., all of Cont 1 to Cont 3 or all of RA-1 to RA-3) as a population, when representing a relationship between the flatness when the Δr was 15 μm and the ratio of the cells as a histogram, an apparent shift was found (FIG. 7).

TABLE 3

|  | Undifferentiated iPS cells | | | Retinoic acid-added iPS cells | | |
| --- | --- | --- | --- | --- | --- | --- |
|  | Cont-1 | Cont-2 | Cont-3 | RA-1 | RA-2 | RA-3 |
| Flatness | −2.399 | −2.336 | −2.519 | −1.392 | −1.517 | −1.425 |
| Standard deviation | 0.294 | 0.218 | 0.221 | 0.379 | 0.292 | 0.298 |

Example 4

Figure 8:
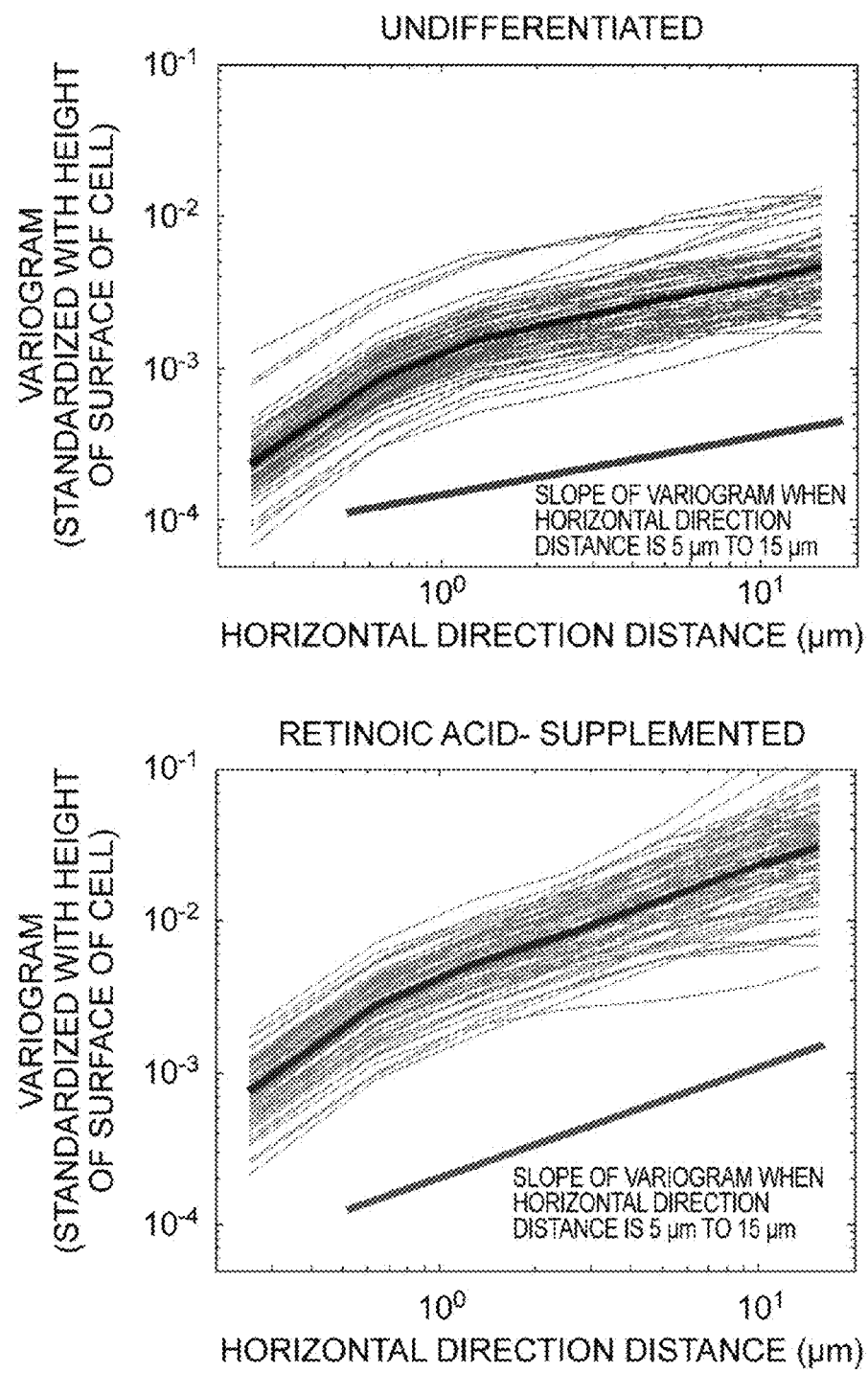
FIG. 8 is views showing the flatness of undifferentiated iPS cells and iPS cells cultured by supplementing retinoic acid in Example 4. The flatness was calculated as a slope of variograms when the $\Delta r$ was within a range of 5 μm to 15 μm, which were standardized with a mean value of height of the surface of the cell. The measurement was performed in a ROI unit within a microscopic visual field.

Under the same condition as that of Example 3, a variogram analysis was performed using a value of MSHD which was standardized with a mean value of height of the surface of the cells, and a slope of the variogram when the Δr was within a range of 5 μm to 15 μm was calculated as the flatness, using formula (III) as described above. Then, a statistical analysis was done to perform Student's t-test. The result was shown in Table 4 and FIG. 8. The flatness of the iPS cells cultured by supplementing retinoic acid was markedly higher than the flatness of the undifferentiated iPS cells.

TABLE 4

|  | Undifferentiated iPS cells | | | Retinoic acid-added iPS cells | | |
| --- | --- | --- | --- | --- | --- | --- |
|  | Cont-1 | Cont-2 | Cont-3 | RA-1 | RA-2 | RA-3 |
| Flatness | 0.446 | 0.410 | 0.351 | 0.848 | 0.744 | 0.880 |
| Standard deviation | 0.274 | 0.217 | 0.201 | 0.343 | 0.303 | 0.264 |

Example 5

Except that the sample of the iPS cells for differentiation was cultured in the medium which was replaced with 10% FBS-containing DMEM medium on the fourth day after the seeding but then not replaced until the seventh day after the seeding, the samples of the cells were prepared in the same way as that of Example 1, and the measurement was performed on the seventh day after the seeding.

Figure 9:
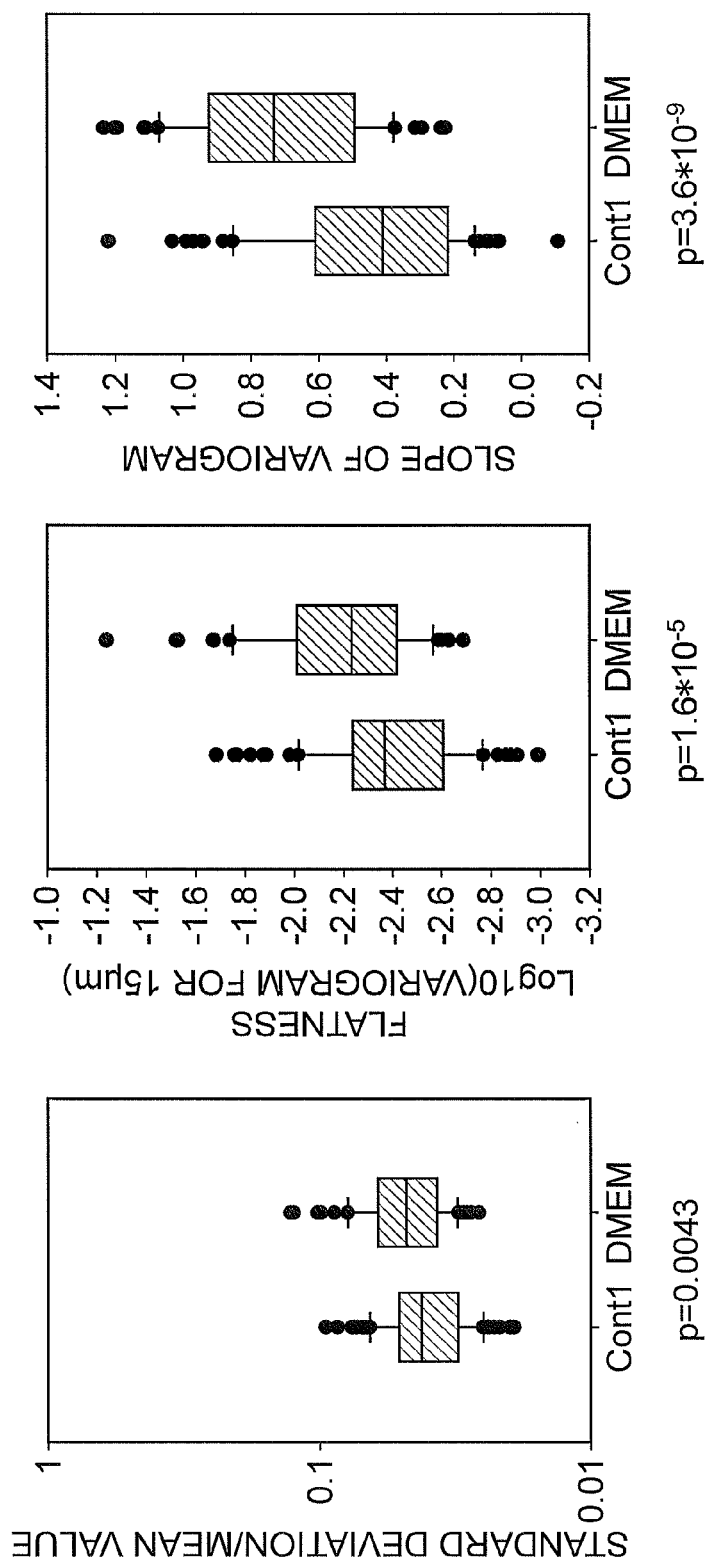
FIG. 9 is views showing the flatness calculated using different approaches for undifferentiated iPS cells and iPS cells cultured in a DMEM medium in Example 5. The measurement was performed in a ROI unit within a microscopic visual field.

In the same way as those of Examples 2 to 4, for each ROI unit within a microscopic visual field, the flatness was calculated as a standard deviation of height of the surface of the cells which was standardized with a mean value of height of the surface of the cells, a value of MSHD when the Δr was 15 μm which was standardized with a mean value of height of the surface of the cells, and a slope of a variogram when the Δr was 5 μm to 15 μm. A statistical analysis was done to perform Student's t-test. The result was shown in Table 5 and FIG. 9. Note that the variogram represents the value of MSHD when the Δr is within a range of 5 μm to 15 μm which is standardized with a mean value of height of the surface of the cells.

TABLE 5

|  |  | Undifferentiated iPS Cont-1 | Cultured iPS in DMEM DMEM-1 |
| --- | --- | --- | --- |
| Standard deviation of height of surface of cells | Flatness | 0.043 | 0.052 |
|  | Standard deviation | 0.015 | 0.021 |
| MSHD (represented by common logarithm) | Flatness | −2.399 | −2.182 |
|  | Standard deviation | 0.294 | 0.304 |
| Slope of variogram | Flatness | 0.446 | 0.720 |
|  | Standard deviation | 0.274 | 0.264 |

Example 6

Figure 10:
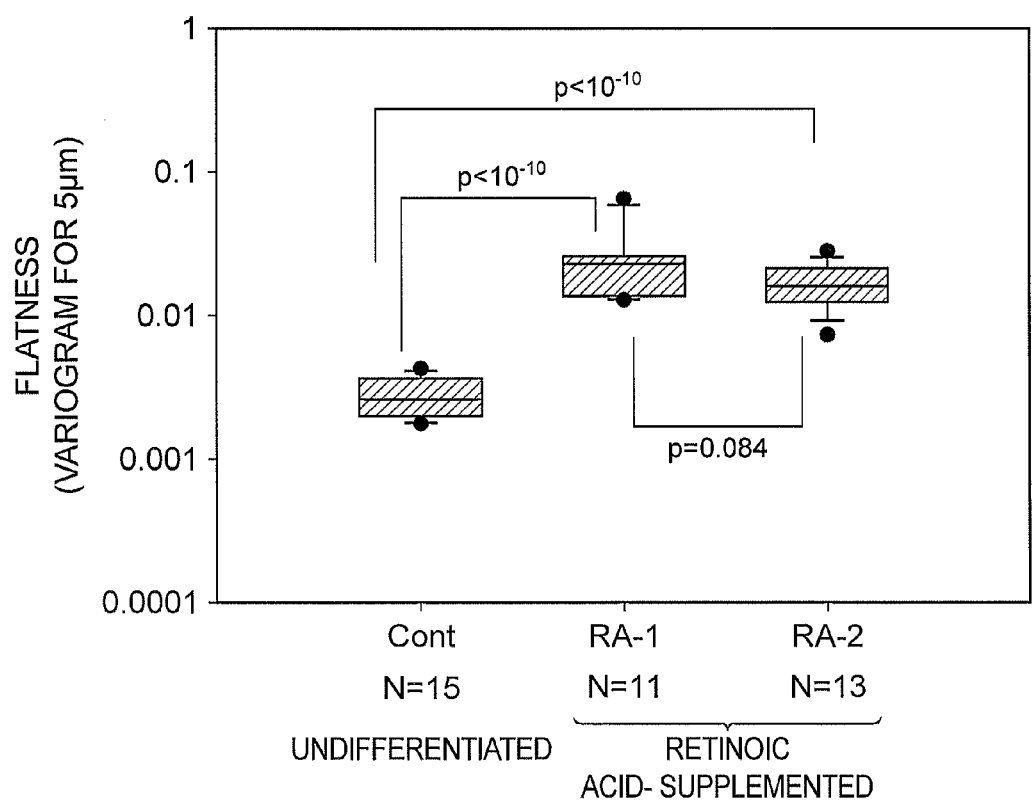
FIG. 10 is a view showing the flatness in Example 6. The measurement was performed in a microscopic visual field unit. The flatness was calculated as a value of MSHD which was standardized with a mean value of height of the surface of the cell. The $\Delta r$ is 5 μm.

By using images shot using each sample in Example 2 of one colony (15 visual fields) for the undifferentiated iPS cells and 2 colonies (11 and 13 visual fields, respectively) for the iPS cells cultured by supplementing retinoic acid, the height of the surface of the cells for each visual field unit was measured using a reflection quantitative phase microscope under the same condition as that of Example 2. A value of MSHD when the Δr was 5 μm was calculated and standardized with a mean value of height of the surface of the cells, then the common logarithm was taken and the flatness was calculated. A statistical analysis was done to perform Student's t-test. The result was shown in Table 6 and FIG. 10. The flatness of the iPS cells cultured by supplementing retinoic acid was markedly higher than the flatness of the undifferentiated iPS cells.

TABLE 6

|  | Undifferentiated iPS | Retinoic acid-added iPS | |
| --- | --- | --- | --- |
|  | Cont-1 | RA-1 | RA-2 |
| Flatness | −2.567 | −1.657 | −1.796 |
| Standard deviation | 0.129 | 0.209 | 0.151 |

What is claimed is:

1. A method comprising the steps of:
   i) measuring flatness of at least one cultured pluripotent stem cell to determine whether the cultured pluripotent stem cell or a cultured pluripotent stem cell population is differentiated by applying a Student's t-test to compare the flatness of the cultured pluripotent stem cell or the cultured pluripotent stem cell population with those of undifferentiated pluripotent stem cells and differentiated cells, and
   ii) identifying and removing at least one cultured pluripotent stem cell that is determined to be differentiated,
   wherein the flatness of the cultured pluripotent stem cell or the cultured pluripotent stem cell population is measured from at least one tomographic image of a three-dimensional image of the cultured pluripotent stem cell or the cultured pluripotent stem cell population,
   wherein the measured flatness is flatness of a surface of the cultured pluripotent stem cell roughly parallel to a bottom surface of the cultured pluripotent stem cell attached to a culture vessel or flatness of a surface of the cultured pluripotent stem cell population roughly parallel to a bottom surface of the cultured pluripotent stem cell population attached to a culture vessel, and
   wherein the measured flatness of a differentiated cell or a differentiated cell population is statistically different from the measured flatness of an undifferentiated pluripotent stem cell or an undifferentiated pluripotent stem cell population.

2. The method according to claim 1, wherein the flatness of the cultured pluripotent stem cell or the cultured pluripotent stem cell population is measured from a single cultured pluripotent stem cell.

3. The method according to claim 1, wherein the flatness of the cultured pluripotent stem cell or the cultured pluripotent stem cell population is determined by calculating a standard deviation of height of the surface of one cultured pluripotent stem cell or the surface of the cultured pluripotent stem cell population,
   wherein the height of the surface of one cultured pluripotent stem cell is a distance from a bottom surface of the cultured pluripotent stem cell attached to a culture vessel to the surface of the cultured pluripotent stem cell not attached to the culture vessel and roughly parallel to the bottom surface, and
   wherein the height of the surface of the cultured pluripotent stem cell population is a distance from a bottom surface of the cultured pluripotent stem cell population attached to a culture vessel to the surface of the cultured pluripotent stem cell population not attached to the culture vessel and roughly parallel to the bottom surface.

4. The method according to claim 3, wherein the calculated value for the flatness is standardized with a mean value of height of the surface of one cultured pluripotent stem cell or the surface of the cultured pluripotent stem cell population.

5. The method according to claim 1, wherein the flatness of the cultured pluripotent stem cell or the cultured pluripotent stem cell population is determined by calculating a mean square height difference (MSHD) represented by formula (1):

$$\text{MSHD}(\Delta r) = \langle (z(x_1,y_1) - z(x_2,y_2))^2 \rangle \quad (\text{I})$$

wherein $z(x_1, y_1)$ is a height of a surface of the cultured pluripotent stem cell or the cultured pluripotent stem cell population at a first point, $z(x_2, y_2)$ is a height of a surface of the cultured pluripotent stem cell or the cultured pluripotent stem cell population at a second point, and $\langle \rangle$ is an ensemble average, wherein $\Delta r$ is distance in a horizontal direction between the first and the second point, and wherein $(x_1, y_1)$ and $(x_2, y_2)$ are in any combination that satisfies formula (II):

$$\Delta r = ((x_1-x_2)^2 + (y_1-y_2)^2)^{1/2} \quad (\text{II}).$$

6. The method according to claim 1, wherein the flatness of the cultured pluripotent stem cell or the cultured pluripotent stem cell population is determined using a reflection quantitative phase microscope.

7. The method according to claim 1, wherein the flatness of the cultured pluripotent stem cell or the cultured pluripotent stem cell population is determined in a microscopic visual field unit.

8. The method according to claim 7, wherein the flatness of the cultured pluripotent stem cell or the cultured pluripotent stem cell population is determined by calculating a standard deviation of height of the surface of one cultured pluripotent stem cell or the surface of the cultured pluripotent stem cell population,
   wherein the height of the surface of one cultured pluripotent stem cell is a distance from a bottom surface of the cultured pluripotent stem cell attached to a culture vessel to the surface of the cultured pluripotent stem cell not attached to the culture vessel and roughly parallel to the bottom surface, and
   wherein the height of the surface of the cultured pluripotent stem cell population is a distance from a bottom surface of the cultured pluripotent stem cell population attached to a culture vessel to the surface of the cultured pluripotent stem cell population not attached to the culture vessel and roughly parallel to the bottom surface.

9. The method according to claim 7, wherein the flatness of the cultured pluripotent stem cell or the cultured pluripotent stem cell population is determined by calculating a mean square height difference (MSHD) represented by formula (1):

$$\text{MSHD}(\Delta r) = \langle (z(x_1,y_1) - z(x_2,y_2))^2 \rangle \quad (\text{I})$$

wherein $z(x_1, y_1)$ is a height of a surface of the cultured pluripotent stem cell or the cultured pluripotent stem cell population at a first point, $z(x_2, y_2)$ is a height of a surface of the cultured pluripotent stem cell or the cultured pluripotent stem cell population at a second point, and $\langle \rangle$ is an ensemble average, wherein $\Delta r$ is distance in a horizontal direction between the first and the second point, and wherein $(x_1, y_1)$ and $(x_2, y_2)$ are in any combination that satisfies formula (II):

$$\Delta r = ((x_1-x_2)^2 + (y_1-y_2)^2)^{1/2} \quad (\text{II}).$$

10. The method according to claim 7, wherein the calculated value for the flatness is standardized with a mean value of height of the surface of one cultured pluripotent stem cell or the surface of the cultured pluripotent stem cell population.

11. The method according to claim 7, wherein the flatness of the cultured pluripotent stem cell or the cultured pluripotent stem cell population is determined using a reflection quantitative phase microscope.

12. The method according to claim 1, wherein the flatness of the cultured pluripotent stem cell or the cultured pluripotent stem cell population is determined in a region of interest unit within a microscopic visual field.

13. The method according to claim 12, wherein the flatness of the cultured pluripotent stem cell or the cultured pluripotent stem cell population is determined by calculating a standard deviation of height of the surface of one cultured pluripotent stem cell or the surface of the cultured pluripotent stem cell population,
  wherein the height of the surface of one cultured pluripotent stem cell is a distance from a bottom surface of the cultured pluripotent stem cell attached to a culture vessel to the surface of the cultured pluripotent stem cell not attached to the culture vessel and roughly parallel to the bottom surface, and
  wherein the height of the surface of the cultured pluripotent stem cell population is a distance from a bottom surface of the cultured pluripotent stem cell population attached to a culture vessel to the surface of the cultured pluripotent stem cell population not attached to the culture vessel and roughly parallel to the bottom surface.

14. The method according to claim 12, wherein the flatness of the cultured pluripotent stem cell or the cultured pluripotent stem cell population is determined by calculating a mean square height difference (MSHD) represented by formula (1):

$$\text{MSHD}(\Delta r) = \langle (z(x_1, y_1) - z(x_2, y_2))^2 \rangle \tag{I}$$

wherein $z(x_1, y_1)$ is a height of a surface of the cultured pluripotent stem cell or the cultured pluripotent stem cell population at a first point, $z(x_2, y_2)$ is a height of a surface of the cultured pluripotent stem cell or the cultured pluripotent stem cell population at a second point, and $\langle \rangle$ is an ensemble average, wherein $\Delta r$ is distance in a horizontal direction between the first and the second point, and wherein $(x_1, y_1)$ and $(x_2, y_2)$ are in any combination that satisfies formula (II):

$$\Delta r = ((x_1 - x_2)^2 + (y_1 - y_2)^2)^{1/2} \tag{II}$$

15. The method according to claim 12, wherein the calculated value for the flatness is standardized with a mean value of height of the surface of one cultured pluripotent stem cell or the surface of the cultured pluripotent stem cell population.

16. The method according to claim 12, wherein the flatness of the cultured pluripotent stem cell or the cultured pluripotent stem cell population is determined using a reflection quantitative phase microscope.

* * * * *